(12) United States Patent
Wang et al.

(10) Patent No.: US 7,824,867 B2
(45) Date of Patent: Nov. 2, 2010

(54) RAPID ELISA PROCESSES AND RELATED COMPOSITIONS

(75) Inventors: Zhuying Wang, Monmouth, NJ (US); Fang Liang Zhang, Fanwood, NJ (US); Tao Bai, Nanjing (CN)

(73) Assignee: GenScript Holdings (Hong Kong) Limited, Piscataway, NJ (US)

( * ) Notice: Subject to any disclaimer, the term of this patent is extended or adjusted under 35 U.S.C. 154(b) by 119 days.

(21) Appl. No.: 12/119,793

(22) Filed: May 13, 2008

(65) Prior Publication Data

US 2008/0311602 A1    Dec. 18, 2008

Related U.S. Application Data

(60) Provisional application No. 60/929,206, filed on Jun. 18, 2007.

(51) Int. Cl.
*G01N 33/53*    (2006.01)
(52) U.S. Cl. .................. 435/7.1; 436/507; 436/513
(58) Field of Classification Search ........................ None
See application file for complete search history.

(56) References Cited

U.S. PATENT DOCUMENTS

| | | | |
|---|---|---|---|
| 6,498,016 B1 | 12/2002 | Nahar et al. | |
| 6,656,715 B1 * | 12/2003 | Vreeland | 435/189 |
| 2007/0134256 A1 * | 6/2007 | Lai et al. | 424/159.1 |

OTHER PUBLICATIONS

Takahashi et al. (J. Pesticide Sci 1998 vol. 23, p. 386-391).*
E. Engvall et al., Enzyme-linked immunosorbent assay (ELISA) Quantitative assay of immunoglobulin G, Immunochemistry (1971) vol. 8, No. 9, pp. 871-874.
J. Y. Douillard et al., Enzyme-linked immunosorbent assay for screening monoclonal antibody production using enzyme-labeled second antibody, Methods in Enzymology, (1983) vol. 92, pp. 168-174.
H. Hjelm et al., Immunologically active and structurally similar fragments of protein A from staphylococcus aureus, Eur. J. Biochem. (1975) vol. 57, No. 2, pp. 395-403.
W. Van Raamsdonk et al., Detection of antigens and antibodies by an immuno-peroxidase method applied on thin longitudinal sections of SDS-polyacrylamide gels, J. Immunol. Methods. (1977) vol. 17, pp. 337-348.
W. N. Burnette, "Western blotting": Electrophoretic transfer of proteins from sodium dodecyl sulfate-polyacrylamide gels to unmodified nitrocellulose and radioiodinated protein A. Analytical Biochemistry, (1981) vol. 112, No. 2, pp. 195-203.
R. Hawkes et al., A dot-immunobinding assay for monoclonal and other antibodies, Analytical Biochemistry. (1982) vol. 119, pp. 142-147.
L. Björck et al., Purification and some properties of streptococcal protein G, a novel IgG-binding reagent, J. Immunol. (1984) vol. 133, No. 2, pp. 969-974.
D.M. Boorsma, Direct immunoenzyme double staining applicable for monoclonal antibodies, Histochemistry (1984) vol. 80, No. 2, pp. 103-106.
K. Osther et al., The quick western blot, a novel transportable 50-minute HIV-1 antibody test, Transplantation (1989) vol. 47, No. 5, pp. 834-838.
K.X. Jacobsen et al., Vibration enhancement of slide-mounted immunofluorescence staining, J. Neurosci. Methods. (2004) vol. 137, pp. 71-77.

* cited by examiner

*Primary Examiner*—Jacob Cheu
(74) *Attorney, Agent, or Firm*—Eckert Seamans Cherin & Mellott, LLC

(57) ABSTRACT

The present invention provides improved and rapid detection methods for an antigen such as a chemical compound, a peptide, a nucleic acid, or a protein released from cells or virus particles in situ. The detection time for an antigen can be dramatically reduced relative to conventional technologies. The technology can particularly be used, for example, to modify and reduce the detection time significantly in traditional ELISA, and also Western blot or Dot blot assays. The improved ELISA method is rapid, economical, reproducible, simple and automatable. Also provided are compositions and kits for using the improved ELISA methods for the rapid detection of antigens.

14 Claims, 6 Drawing Sheets

Classical Direct ELISA

Rabbit anti GST Antibody Titer Determination

A□B □ELISA of the Current Invention;   C□D□ Classical ELISA

|   | BLK | NC | 1k | 2k | 4k | 8k | 16k | 32k | 64k | 128k | 256k | 512k |
|---|---|---|---|---|---|---|---|---|---|---|---|---|
| A | 0.052 | 0.064 | 1.742 | 1.546 | 1.270 | 0.915 | 0.670 | 0.402 | 0.253 | 0.166 | 0.109 | 0.099 |
| B | 0.050 | 0.057 | 1.668 | 1.495 | 1.242 | 0.916 | 0.601 | 0.397 | 0.233 | 0.147 | 0.099 | 0.095 |
| C | 0.048 | 0.076 | 0.854 | 0.817 | 0.693 | 0.558 | 0.429 | 0.318 | 0.249 | 0.165 | 0.124 | 0.111 |
| D | 0.044 | 0.059 | 0.819 | 0.789 | 0.685 | 0.554 | 0.434 | 0.301 | 0.214 | 0.144 | 0.108 | 0.094 |

RAPID ELISA PROCESSES AND RELATED COMPOSITIONS

CROSS REFERENCE TO RELATED APPLICATIONS

The present application claims priority to U.S. Provisional Application No. 60/929,206, filed Jun. 18, 2007, which is incorporated herein by reference.

BACKGROUND OF THE INVENTION

1. Field of the Invention

The present invention relates to a detection method for an antigen such as a chemical compound, a peptide, a protein, an RNA, a DNA, a cell (proteins released in situ), or a virus particle (proteins released in situ). In particular, the present invention provides a method and composition useful for performing ELISA assays, which also can be used for Western blot and Dot blot assays.

2. Description of the Prior Art

Immunological methods have become important tools useful for detecting antigens including, for example, peptides, proteins, nucleic acids, biological cells, and virus particles. A wide variety of methods have been developed for the detection or quantitation of antigens. Among them, Western Blot, Dot Blot, ELISA and Immunohistology are the four most commonly used methods.

Enzyme-linked Immunosorbent Assays (ELISAs), which combine the high specificity of antibodies with the high sensitivity of enzyme assays by using antibodies or antigens coupled to an easily assayed enzyme that possesses a high turnover number such as alkaline phosphatase (AP) or horseradish peroxidase (HRP), are very useful tools both for determining antibody concentrations (antibody titer) in sera as well as for detecting the presence of antigen.

There are two main variations on this method: ELISA can be used to detect the presence of antigens that are recognized by a detection agent or it can be used to test for detection agents that recognize an antigen. There are many different types of ELISAs. Four of the most common types of ELISA are "Direct ELISA," "Indirect ELISA," "Sandwich ELISA" and Cell-based ELISA (C-ELISA).

A conventional direct ELISA (FIG. 1) is comprised of the following steps: (i) coating a solid phase with an antigen dissolved in a coating buffer; (ii) incubating the solid phase from Step (i) with a blocking reagent for 1 hour to block non-specific binding sites on the solid phase; (iii) washing the solid phase from Step (ii) three times with PBS or PBST for 1 min each; (iv) incubating the solid phase from Step (iii) with a primary detection agent which binds to the antigen; (v) washing the solid support from Step (iii) five times for 1 min each in PBS or PBST to remove the non-specifically bound primary detection agent; and (vi) using a detection system such as UV, fluorescence, chemiluminescence or other detection methods to detect the bound primary detection agent. The primary detection agent can be, without limitation, a detection agent linked (coupled) to a fluorescent dye, or a reporter enzyme such as alkaline phosphatase (AP) or horseradish peroxidase (HRP), which can convert a colorless substrate to a colored product whose optical densities can be measured on an ELISA plate reader at target wavelengths.

A conventional indirect ELISA (FIG. 3) is comprised of the following steps: (i) coating a solid phase with an antigen dissolved in a coating buffer; (ii) incubating the solid phase from Step (i) with a blocking reagent for 1 hour to block non-specific binding sites on the solid phase; (iii) washing the solid phase from Step (ii) three times with PBS or PBST for 1 min each; (iv) incubating the solid phase from Step (iii) with a primary detection agent diluted in a solution for 1 hour; (v) washing the solid support from Step (iv) three times for 1 min in PBS or PBST to remove the non-specifically bound primary detection agent; (vi) incubating the solid support from step (v) with a secondary detection agent diluted in a solution for 1 hour; (vii) washing the solid support from Step (vi) five times for 1 min each in PBS or PBST to remove the non-specifically bound secondary detection agent; and (viii) using a detection system such as UV, fluorescence, chemiluminescence or other methods to detect the bound secondary detection agent. The secondary detection agent binds the primary detection agent. The secondary detection agent can be, without limitation, a detection agent linked (coupled) to a reporter enzyme such as alkaline phosphatase (AP) or horseradish peroxidase (HRP), which can convert a colorless substrate to a colored product whose optical densities can be measured on an ELISA plate reader at target wavelengths.

The complete direct ELISA procedure involves at least three incubation steps: the first is incubation between the solid support and the antigen; the second is incubation between the solid support and the blocking reagent; and the third one is incubation between the solid support and the primary detection agent. The incubation step is a two-phase reaction and involves the binding reaction between the antigen on the solid support and the detection agent.

The complete indirect ELISA procedure involves at least four incubation steps: the first is incubation between the solid support and an antigen; the second is incubation between the solid support and the blocking reagent; the third one is incubation between the solid support and the primary detection agent; and the fourth is incubation between the solid support and the secondary detection agent. The incubation step is a two-phase reaction and involves the binding reaction between the antigen on the solid support and the detection agent.

In a conventional direct ELISA, the first incubation step, antigen coating, takes at least 2 hours and each other incubation step takes about 1 hour. A conventional direct ELISA, as described above, therefore, takes at least 4 hours.

In a conventional indirect ELISA, the first incubation step, antigen coating, takes at least 2 hours and each other incubation step takes about 1 hour. A conventional indirect ELISA, as described above, will take at least 5 hours. Because conventional direct and indirect ELISA consumes valuable time, there is a need for a simple and rapid process to address these conventional time-consuming assays.

The cell-based ELISA (C-ELISA) is a moderate throughput format for detecting and quantifying cellular proteins including post-translational modifications associated with cell activation (e.g., phosphorylation and degradation). Cells are plated, treated according to experimental requirements, fixed directly in the wells, and then permealized. After permealizing, fixed cells are treated similar to a conventional immunoblot, including blocking, incubation with a first antibody, washing, incubation with a second antibody, addition of chemilumescent substrates and development.

In 1971, Engvall and Perlmann (Immunochem., 8:871-874, 1971) coined the term "enzyme-linked immunosorbent assay," which is better known by the acronym "ELISA", to describe an enzyme-based immunoassay method which is very useful for measuring antigen concentrations. Since then, ELISA has not only become one of the most commonly used methods for protein and antibody detection and identification but also the basic immunoassay upon which many of the modern assays are based.

A rapid method for microwave mediated enzyme-linked immunosorbent assay (M-ELISA) (U.S. Pat. No. 6,498,016) was developed to perform ELISA rapidly. However, this procedure requires a carefully-controlled microwave which needs optimization.

Although there have been substantive improvements in all of these immuno-detection methods, including the quality of reagents, solid phase plates and plastics, microplate readers, washers, and statistical software, the basic methodology has remained virtually unchanged.

SUMMARY OF THE INVENTION

The present invention provides improved methods and compositions for performing a rapid enzyme-linked immunosorbent assay (ELISA).

In an aspect of the present invention, there is provided a method for performing a direct rapid enzyme-linked immunosorbent assay (ELISA), comprising the steps of coating a solid phase with an antigen dissolved in a quick coating buffer for between about two to twenty minutes, preferably for about five minutes; blocking the solid phase with a blocking reagent dissolved in a quick blocking buffer for between about two to ten minutes, preferably for about five minutes; incubating the solid phase with a primary detection agent in solution; washing the solid phase to remove any unbound primary detection agent; and detecting the presence of an agent bound on the solid phase with a detection system that detects the bound primary detection agent.

In another aspect of the present invention, there is provided a method for performing an indirect rapid enzyme-linked immunosorbent assay (ELISA), comprising coating a solid phase with an antigen dissolved in a quick coating buffer for between about two to twenty minutes, preferably for about five minutes; blocking the solid phase with a blocking reagent dissolved in a quick blocking buffer for between about two to ten minutes, preferably for about five minutes; incubating the solid phase with a primary detection agent in solution and then washing the solid phase to remove any unbound primary detection agent; incubating the solid phase with a secondary detection agent and then washing the solid phase to remove any unbound secondary detection agent; and detecting the presence of an agent bound on the solid phase with a detection system that detects the bound secondary detection agent.

In a further aspect of the present invention, there is provided a method for performing an indirect rapid enzyme-linked immunosorbent assay (ELISA), comprising coating a solid phase with an antigen dissolved in a quick coating buffer for between about two to twenty minutes, preferably for about five minutes; blocking the solid phase with a blocking reagent dissolved in a quick blocking buffer for between about two to ten minutes, preferably for about five minutes; incubating the solid phase simultaneously with a primary detection agent and a secondary detection agent and then washing the solid phase to remove any unbound primary detection agent and secondary detection agent; and detecting the presence of an agent bound on the solid phase with a detection system that detects the bound secondary detection agent.

In another aspect of the present invention, there is provided a method for performing an indirect rapid enzyme-linked immunosorbent assay (ELISA), comprising coating a solid phase with an antigen dissolved in a quick coating buffer for between about two to twenty minutes, preferably for about five minutes; blocking the solid phase with a blocking reagent dissolved in a quick blocking buffer for between about two to ten minutes, preferably for about five minutes; incubating the solid phase with a primary detection agent in solution and then washing the solid phase to remove any unbound primary detection agent; incubating the solid phase with a secondary detection agent and then washing the solid phase to remove any unbound secondary detection agent; incubating the solid phase with a tertiary detection agent and then washing the solid phase to remove any unbound tertiary detection agent; and detecting the presence of an agent bound on the solid phase with a detection system that detects the bound tertiary detection agent.

In still another aspect of the present invention, there is provided a method for performing an indirect rapid enzyme-linked immunosorbent assay (ELISA), comprising coating a solid phase with an antigen dissolved in a quick coating buffer for between about two to twenty minutes, preferably for about five minutes; blocking the solid phase with a blocking reagent dissolved in a quick blocking buffer for between about two to ten minutes, preferably for about five minutes; incubating the solid phase simultaneously with a primary detection agent, a secondary detection agent and a tertiary detection agent and then washing the solid phase to remove any unbound primary, secondary and tertiary detection agent; and detecting the presence of an agent bound on the solid phase with a detection system that detects the bound tertiary detection agent.

In still another aspect of the present invention, there is provided a method for performing a rapid cell-based enzyme-linked immunosorbent assay (C-ELISA), comprising lysing cells in a quick lysis and coating buffer; coating a solid phase with cellular proteins released in situ in the quick lysis and coating buffer for about two to twenty minutes, preferably for about five to ten minutes; blocking the solid phase with a blocking reagent dissolved in a quick blocking buffer for between about two to ten minutes, preferably for about five minutes; incubating the solid phase with a primary detection agent in solution; washing the solid phase to remove any unbound primary detection agent; and detecting the presence of an agent bound on the solid phase with a detection system that detects the bound primary detection agent.

In still another aspect of the present invention, there is provided a method for performing a rapid cell-based enzyme-linked immunosorbent assay (C-ELISA), comprising lysing cells in a quick lysis and coating buffer; coating a solid phase with cellular proteins released in situ in the quick lysis and coating buffer for about two to twenty minutes, preferably for about five to ten minutes; blocking the solid phase with a blocking reagent dissolved in a quick blocking buffer for between about two to ten minutes, preferably for about five minutes; incubating the solid phase with a primary detection agent in solution and then washing the solid phase to remove any unbound primary detection agent; incubating the solid phase with a secondary detection agent and then washing the solid phase to remove any unbound secondary detection agent; and detecting the presence of an agent bound on the solid phase with a detection system that detects the bound secondary detection agent.

In still another aspect of the present invention, there is provided a method for performing a rapid cell-based enzyme-linked immunosorbent assay (C-ELISA), comprising lysing cells in a quick lysis and coating buffer; coating a solid phase with cellular proteins released in situ in the quick lysis and coating buffer for about two to twenty minutes, preferably for about five to ten minutes; blocking the solid phase with a blocking reagent dissolved in a quick blocking buffer for between about two to ten minutes, preferably for about five minutes; incubating the solid phase simultaneously with a primary detection agent and a secondary detection agent; washing the solid phase to remove any unbound primary and secondary detection agent; and detecting the presence of an agent bound on the solid phase with a detection system that detects the bound secondary detection agent.

In another aspect of the present invention, there is provided a method for performing an indirect rapid cell-based enzyme-linked immunosorbent assay (C-ELISA), comprising lysing cells in a quick lysis and coating buffer; coating a solid phase with cellular proteins released in situ in the quick lysis and coating buffer for two to twenty minutes, preferably for about five minutes; blocking the solid phase with a blocking reagent dissolved in a quick blocking buffer for between about two to ten minutes, preferably for about five minutes; incubating the solid phase with a primary detection agent in solution and then washing the solid phase to remove any unbound primary detection agent; incubating the solid phase with a secondary detection agent and then washing the solid phase to remove any unbound secondary detection agent; incubating the solid phase with a tertiary detection agent and then washing the solid phase to remove any unbound tertiary detection agent; and detecting the presence of an agent bound on the solid phase with a detection system that detects the bound tertiary detection agent.

In still a further aspect of the present invention, there is provided a method for performing a rapid cell-based enzyme-linked immunosorbent assay (C-ELISA), comprising lysing cells in a quick lysis and coating buffer; coating a solid phase with cellular proteins released in situ in the quick lysis and coating buffer for about two to twenty minutes, preferably for about five to ten minutes; blocking the solid phase with a blocking reagent dissolved in a quick blocking buffer for between about two to ten minutes, preferably for about five minutes; incubating the solid phase simultaneously with a primary detection agent, a secondary detection agent and a tertiary detection agent; washing the solid phase to remove any unbound primary, secondary and tertiary detection agent; and detecting the presence of an agent bound on the solid phase with a detection system that detects the bound tertiary detection agent.

In still another aspect of the present invention, there is provided a rapid enzyme-linked immunosorbent assay (ELISA), comprising a quick coating buffer and a blocking reagent in a quick blocking buffer. The quick coating buffer is comprised of water and a metal hydroxide such as, without limitation, sodium hydroxide, potassium hydroxide or rubidium hydroxide. Preferably, the metal hydroxide is sodium hydroxide. The concentration of the metal hydroxide can range from between about 0.004 g/l to 40 g/l of buffer, and preferably is about 4 g/l of buffer. The pH of the quick coating buffer can range from between about 10.0 to 14.0, and preferably is about 13.0. The quick blocking buffer is comprised of water and a metal hydroxide selected from the group consisting of sodium hydroxide, potassium hydroxide and rubidium hydroxide, and preferably is potassium hydroxide. The concentration of the metal hydroxide can range from between about 0.0056 g/l to 56 g/l of buffer, and preferably is about 5.6 g/l of buffer. The pH of the quick blocking buffer can range from between about 10.0 to 14.0, and preferably is about 13.0.

In still a further aspect of the present invention, there is provided a kit for performing a rapid enzyme-linked immunosorbent assay (ELISA), a western blot assay or a dot blot assay, comprising a quick coating buffer and a blocking reagent dissolved in a quick blocking buffer. The blocking reagent can include, without limitation, non-fat milk, casein, bovine serum albumin, fish gelatin or other suitable chemical reagents known in the art. The quick coating buffer is comprised of water and a metal hydroxide such as, without limitation, sodium hydroxide, potassium hydroxide or rubidium hydroxide. Preferably, the metal hydroxide is sodium hydroxide. The concentration of the metal hydroxide can range from between about 0.004 g/l to 40 g/l of buffer, and preferably is about 4 g/l of buffer. The pH of the quick coating buffer can range from between about 10.0 to 14.0, and preferably is about 13.0. The quick blocking buffer is comprised of water and a metal hydroxide selected from the group consisting of sodium hydroxide, potassium hydroxide and rubidium hydroxide, and preferably is potassium hydroxide. The concentration of the metal hydroxide can range from between about 0.0056 g/l to 56 g/l of buffer, and preferably is about 5.6 g/l of buffer. The pH of the quick blocking buffer can range from between about 10.0 to 14.0, and preferably is about 13.0.

An object of the present invention, therefore, is to provide improved rapid direct and indirect ELISA methods for the detection and quantification of antibodies by using an improved coating buffer. Accordingly, the coating time can be reduced from more than two hours to about five minutes.

Another object of the present invention is to provide improved rapid direct and indirect ELISA methods for the detection and quantification of antibodies by using an improved blocking reagent. Accordingly, the blocking time can be reduced from one hour to about five minutes.

Still another object of the invention is to provide a novel and rapid cell-based ELISA (C-ELISA) method for the detection and quantification of proteins released in situ from cells by using a novel cell lysis and coating reagent, in which the cells are lyzed, the cellular proteins are released and coated onto the surface of plate wells at the same time in a single buffer in as little as five minutes. This removes both the cell fixing step, cell permealizing step and the wash steps related to those two steps.

It is a further object of the invention to provide an improved rapid direct and indirect ELISA method for the detection and quantification of antibodies by using both the improved coating buffer and the blocking reagents. Accordingly, the time can be reduced from more than four hours to about two hours or less (e.g., to about one hour).

A further object of the present invention is to provide an improved rapid indirect ELISA method for the detection and quantification of antibodies by integrating conventional indirect ELISA containing two steps into a one step method, and thus providing a more efficient process.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
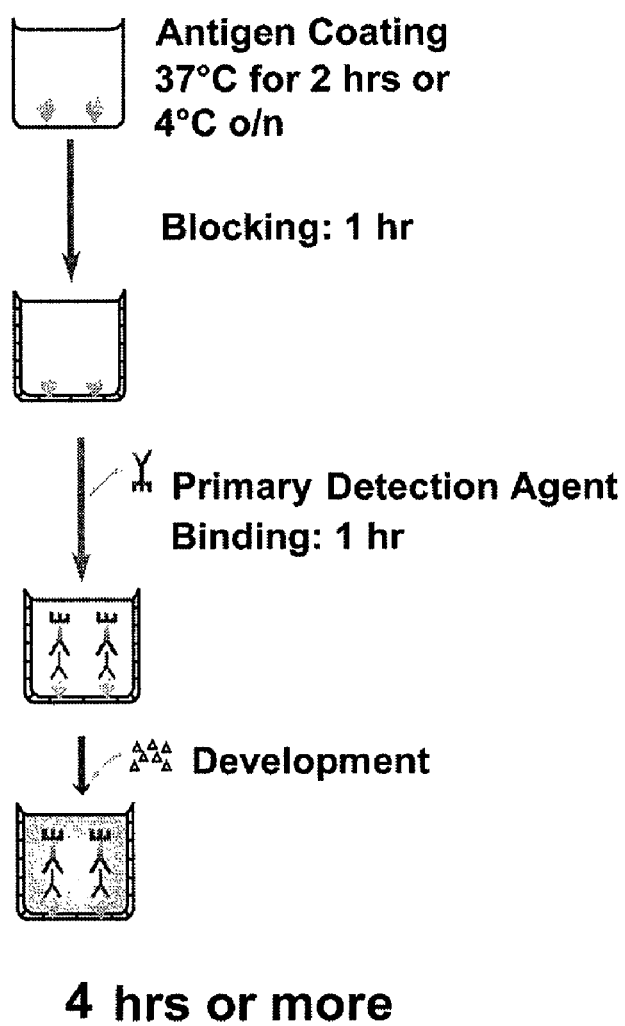
FIG. 1 schematically illustrates procedures of a classical direct ELISA.

Unless defined otherwise, all technical and scientific terms used herein have the same meaning as is commonly understood by one of ordinary skill in the art to which this invention pertains. All publications and patents referred to herein are incorporated by reference.

The invention provides methods and compositions useful for performing antigen or antibody detection or diagnostics using ELISA. In one aspect, the invention provides a significant improvement over conventional ELISA techniques. The invention provides a method whereby several steps in a classical ELISA procedure can be performed or completed in a few minutes instead of hours. The invention also provides a method whereby several steps in a classical ELISA procedure time can be combined into one step or two steps. The methods of the invention greatly reduce the time for detection assays as well as associated costs.

As used herein "antigen" and "antibody" are to be taken in their broadest context. An "antigen" can be any molecule, cell, virus, or particle. For example, an antigen includes, but is not limited to, a chemical molecule, a peptide molecule, a protein molecule, an RNA molecule, a DNA molecule, a traditional antibody, e.g., two heavy chains and two light chains, a recombinant antibody or fragment, a bacterial cell, a virus particle, a cell, a particle, and a product comprising crosslinking any two or more of the above.

An antigen can be in a pure form, or it can exist in a mixture. An antigen can be in a modified form (e.g., modified by chemicals) or can be in an unmodified form.

Reference herein to an "antibody" is to be taken in its broadest context. "An antibody" is a polypeptide that binds to "an antigen." An antibody includes, but is not limited to, a traditional antibody, a fragment of a traditional antibody containing an antigen binding site, a recombinant antibody containing an antigen binding site, a protein which binds to an antigen, and a product comprising crosslinking any two or more of the above.

An antibody can be in a pure form, or it can exist in a mixture. An antibody can be in a modified form (e.g., modified by a chemical) or can be in an unmodified form.

The term "detection agent" refers to an agent that is used to detect an antigen or antibody. A detection agent can be either an "antigen" or an "antibody." A detection agent can be either a labeled "antigen" or "antibody" or an unlabeled "antigen" or "antibody." Suitable labeling methods that can be used in the present invention include, without limitation, isotope labeling, chemical modification, enzyme conjugation, fluorescent dye labeling, luminescence and other labeling methods commonly known by those skilled in the art. Therefore, a detection agent includes, but is not limited to, a chemical molecule, a peptide molecule, a protein molecule, an RNA molecule, a DNA molecule, a traditional antibody, a fragment of a traditional antibody containing an antigen binding site, a recombinant antibody containing an antigen binding site, a protein which binds to an antigen, a bacterial cell, a viral particle, a cell, a particle, and a product comprising crosslinking any two or more of the above.

A detection agent can be in a pure form, or it can be an impure form (e.g., contained in a mixture with other compounds or materials). A detection agent can be in a modified form or can be an unmodified form. According to the order of a "detection agent" used in a method, a "detection agent" can be referred as "a primary detection agent," "secondary detection agent," "a tertiary detection agent" or "a fourth detection agent," and the like.

The term "detection system" refers to a system which can be used to give a readout comprising information related to the quantity or quality of a protein or agent in a sample (e.g., a blot, cell and the like). The choice of a detection system depends on the choice of the detection agent used in a method of the invention. For example, a detection system includes, but is not limited to, X-ray film or other beta/gamma sensitive material if the detection agent is isotope-labeled; if the detection agent is enzyme-labeled, a chemical reaction which can result in color or a chemiluminescence signal that can be detected by, for example, a CCD camera, visual inspection or other device capable of sensing a signal can be used; and if the detection agent is fluorescence-labeled, a fluorescence microscope, a fluorescence cell sorter, a fluorescence scanner or camera can be used.

The invention provides compositions useful in ELISAs. One of the compositions is referred to herein as a quick coating buffer. A quick coating buffer of the invention comprises sodium hydroxide (NaOH) and water. Sodium hydroxide may be substituted with similar elements known in the art that function in solution in substantially the same way. For example, sodium hydroxide can be substituted with potassium hydroxide (KOH) or rubidium hydroxide (RbOH). In one aspect, the quick coating buffer comprises about 0.004 grams to 40 grams per liter of buffer, typically about 4 grams. The quick coating buffer can have a pH in the range of about 10.0 to about 14.0, but typically is about 13.0.

A quick coating buffer of the invention can be bottled and used as typically performed in research and diagnostic laboratories. The quick coating buffer of the present invention is made in sterile water or distilled water that is sterile filtered and/or autoclaved. The quick coating buffer of the invention can be used with ELISA assays. The quick coating buffer can be included in an article of manufacture or kit for use in ELISAs and the like.

The invention provides a second composition useful in ELISAs. The composition is referred to herein as a quick blocking buffer. A quick blocking buffer of the invention comprises potassium hydroxide (KOH) and water. Potassium hydroxide may be substituted with similar elements known in the art that function in solution in substantially the same way. For example, potassium hydroxide can be substituted with sodium hydroxide (NaOH) or rubidium hydroxide (RbOH). In one aspect, the quick blocking buffer comprises about 0.0056 grams to 56 grams per liter of buffer, typically about 5.6 grams. The quick blocking buffer can have a pH in the range of about 10.0 to about 14.0, but typically is about 13.0.

The invention provides a third composition useful in Cell-based ELISA (C-ELISA). The composition is referred to herein as a quick lysis and coating buffer. A quick lysis and coating buffer of the invention comprises potassium hydroxide and water. Potassium hydroxide may be substituted with similar elements known in the art that function in solution in substantially the same way. For example, potassium hydroxide can be substituted with sodium hydroxide (NaOH) or rubidium hydroxide (RbOH). In one aspect, the quick lysis and coating buffer comprises about 0.0056 grams to 56 grams per liter of buffer, typically about 5.6 grams. The quick lysis and coating buffer can have a pH in the range of about 10.0 to about 14.0, but typically is about 13.0.

The quick coating buffer, quick blocking buffer a quick lysis and coating buffer of the present invention can be the same or different.

A quick blocking buffer of the invention can be bottled and used as typically performed in research and diagnostic laboratories. The quick blocking buffer is made in sterile water or distilled water that is sterile filtered and/or autoclaved. The quick blocking buffer of the invention can be used with ELISA assays. The quick blocking buffer can be included in an article of manufacture or kit for use in ELISAs and the like. The quick lysis and coating buffer can also be included in an article of manufacture or kit for use in ELISAs and the like.

The invention mainly can be used in three types of ELISA methods: (1) direct ELISA (antibody capture); (2) indirect ELISA; and (3) Cell-based ELISA.

Direct ELISA (antibody capture assay) is one ELISA method. For detecting or quantitating an antigen or a detection agent (e.g. an antibody) that recognizes an antigen, the antigen is coated on the wells of microtiter plates and incubated with test solutions containing specific detection agents. Usually a reporter-molecule labeled primary detection agent is added to the test solutions containing specific detection agents. After incubation, any unbound labeled primary detection agent is washed away. An incubation with a substrate of reporter enzyme also may be needed. A detection system such as UV, fluorescence, chemiluminescence or other methods is used to detect the bound primary detection agent, which is proportional to the amount of the detection agent to be detected in the test solution.

A conventional direct ELISA is comprised of the steps enumerated in FIG. 1. Three major steps are needed before the final detection step. These steps comprise an antigen coating step, a blocking step and primary detection agent binding step. Each of these steps is necessary in conventional direct ELISA to obtain acceptable results. In conventional direct ELISA, the coating step takes 2 hours at 37° C. or 4° C. o/n. The blocking step takes 1 hour to complete.

The invention provides a direct ELISA that differs from conventional techniques in that each of the coating step and the blocking step of conventional indirect ELISA can be done in just five minutes instead of one or two hours. The new method can greatly cut down the time required for indirect ELISA analysis.

Figure 2:
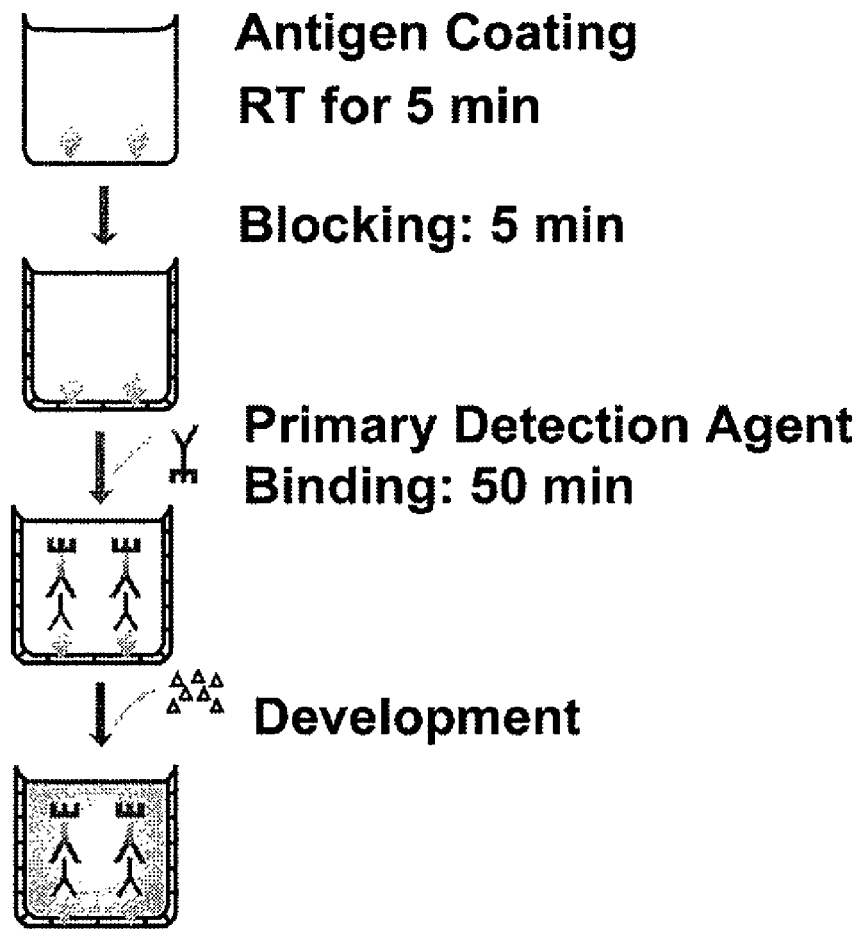
FIG. 2 schematically illustrates procedures of a direct ELISA process of the invention.

As shown in FIG. 2, the direct ELISA method of the invention comprises (i) coating a solid phase with an antigen dissolved in the coating buffer of the invention (five minutes only are needed); (ii) blocking a solid phase with a blocking reagent dissolved in the blocking buffer of the invention (five minutes only are needed); (iii) incubating the solid phase of (ii) with a primary detection agent in a solution followed by (iv) detecting the presence of an agent on the solid phase with a detection system that measures, for example, UV, fluorescence, luminescence, calorimetric or other signal to detect the bound primary detection agent.

Indirect ELISA (detection agent capture assay) is one ELISA method that commonly is used for screening and titer determination of antibodies during the course of their production (Douillard, J. Y. and Hoffman, T., 1983). For detecting a detection agent (e.g. an antibody) that recognizes an antigen, the antigen is coated on the wells of microtiter plates and incubated with test solutions containing specific detection agents. Unbound detection agents are washed away. Then a second incubation with a solution containing a secondary detection agent (e.g. alkaline phosphatase conjugated to protein A, protein G, or antibodies against the detection agents of interest) is needed. After incubation, unbound labeled secondary detection agent is washed away. An incubation with a substrate of reporter enzyme also may be needed. A detection system such as UV, fluorescence, chemiluminescence or other methods is used to detect the bound secondary detection agent, which is proportional to the amount of the detection agent to be detected in the test solution.

Figure 3:
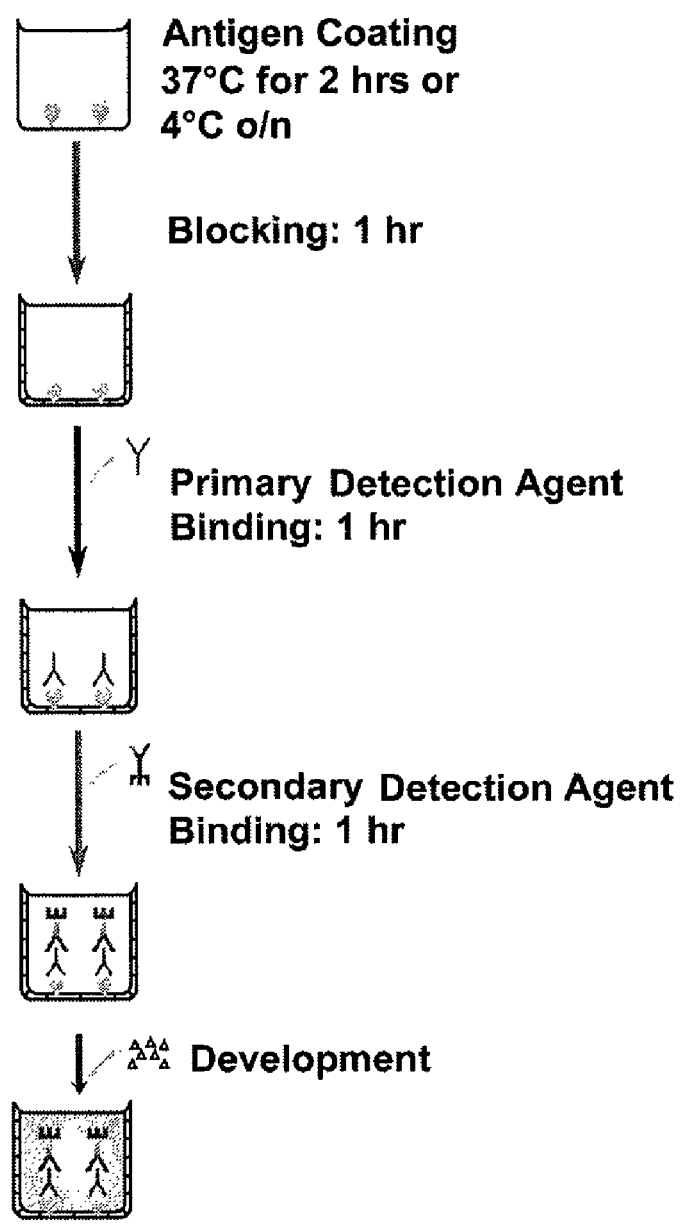
FIG. 3 schematically illustrates procedures of a classical indirect ELISA.

A conventional indirect ELISA is comprised of the steps enumerated in FIG. 3. In conventional indirect ELISA, four major steps are needed before the final detection step. These steps comprise an antigen coating step, a blocking step, primary detection agent binding step and secondary detection agent binding step. Each of these steps is necessary in conventional indirect ELISA to obtain acceptable results. The blocking step blocks remaining hydrophobic binding sites on the solid phase to prevent non-specific protein binding of the detection agent used for detection of the target protein, thereby reducing background and/or preventing false positive results. The primary detection agent and secondary detection agent are incubated with the solid phase separately, and then washed away to avoid non-specific binding and to reduce the background.

The invention provides an indirect ELISA that differs from conventional techniques in that each of the coating step and the blocking step of conventional indirect ELISA can be done in just five minutes instead of one or two hours. The new method can greatly cut down the time required for indirect ELISA analysis.

Figure 4:
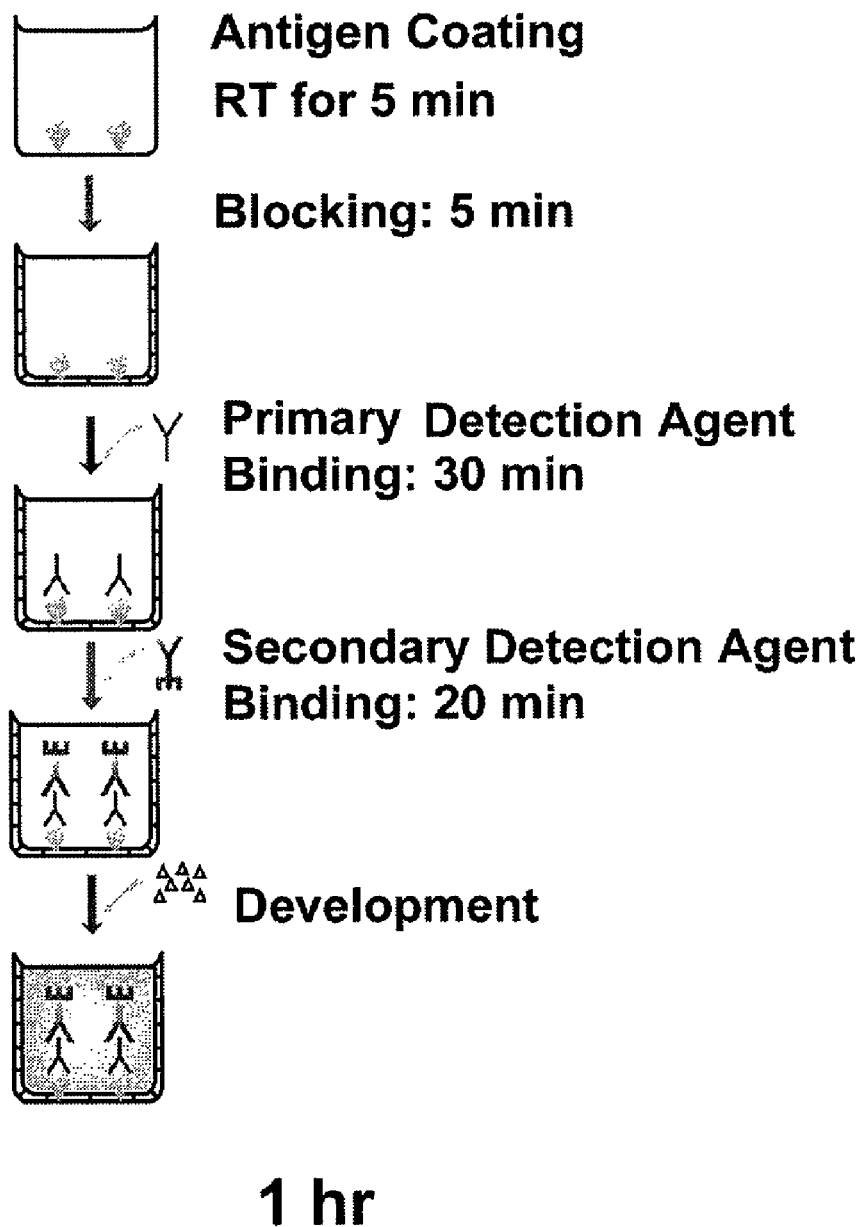
FIG. 4 schematically illustrates procedures of an indirect ELISA process of the invention.

As shown in FIG. 4, the indirect ELISA method of the invention comprises (i) coating a solid phase with an antigen dissolved in the coating buffer of the invention (five minutes only are needed); (ii) blocking a solid phase with a blocking reagent dissolved in the blocking buffer of the invention (five minutes only are needed); (iii) incubating the solid phase of (ii) with a primary detection agent in a solution followed by (iv) incubating the solid phase of (iii) with a secondary detection agent; and (iv) detecting the presence of an agent on the solid phase with a detection system that measures, for example, UV, fluorescence, luminescence, colorimetric or other signal to detect the bound secondary detection agent.

Figure 5:
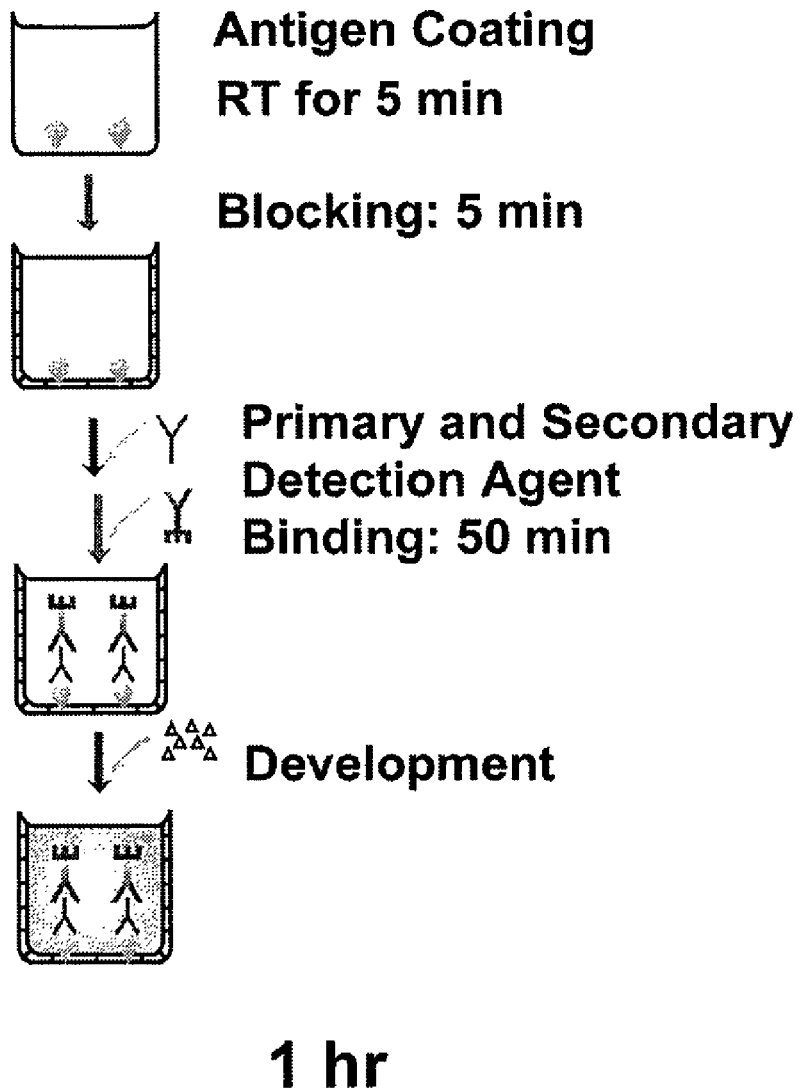
FIG. 5 schematically illustrates procedures of a further indirect ELISA process of the invention.

In another embodiment of the invention, as shown in FIG. 5, the indirect ELISA of the invention comprises (i) coating a solid phase with an antigen dissolved in the coating buffer of the invention (five minutes only are needed); (ii) blocking a solid phase with a blocking reagent dissolved in the blocking buffer of the invention (five minutes only are needed); (iii) incubating the solid phase of (ii) with a primary detection agent and a secondary detection agent; and (iv) detecting the presence of an agent on the solid phase with a detection system that measures, for example, UV, fluorescence, luminescence, calorimetric or other signal to detect the bound secondary detection agent.

In yet another embodiment of the invention, the indirect ELISA method of the invention comprises (i) coating a solid phase with an antigen dissolved in the coating buffer of the invention (five minutes only are needed); (ii) blocking a solid phase with a blocking reagent dissolved in the blocking buffer of the invention (five minutes only are needed); (iii) incubating the solid phase of (ii) with a primary, secondary, and tertiary detection agent in a solution; and (iv) detecting the presence of an agent on the solid phase with a detection system that measures, for example, UV, fluorescence, luminescence, colorimetric or other signal to detect the bound secondary or tertiary detection agent.

A conventional Cell-based ELISA (C-ELISA) is comprised of five major steps before the final detection step. These steps comprise a cell fixing step, a cell permealizing step, a blocking step, primary detection agent binding step and secondary detection agent binding step. Each of these steps is necessary in conventional Cell-based ELISA (C-ELISA) to obtain acceptable results. The cell fixing step will hold cells to the bottom of plate wells so that they will not be washed away in the process. The cell permealizing step will make the cellular proteins available for immunoassays. The blocking step blocks remaining hydrophobic binding sites on the solid phase to prevent non-specific protein binding of the detection agent used for detection of the target protein, thereby reducing background and/or preventing false positive results. The primary detection agent and secondary detection agent are incubated with the solid phase separately, and then washed away to avoid non-specific binding and to reduce the background.

The invention provides a Cell-based ELISA (C-ELISA) that differs from conventional techniques in that a cell fixing step and a cell permealizing step of conventional Cell-based ELISA are replaced by a single lysis and coating in just five to ten minutes. The blocking step of conventional Cell-based ELISA also can be done in just five minutes instead of one or two hours. The improved method of the present invention can greatly cut down the time required for Cell-based ELISA (C-ELISA).

The Cell-based ELISA (C-ELISA) method of the invention comprises (i) lysing cells and coating a solid surface with the cellular proteins released in situ in the lysis and coating buffer of the invention (five to ten minutes only are needed); (ii) blocking a solid phase with a blocking reagent dissolved in the blocking buffer of the invention (five minutes only are needed); (iii) incubating the solid phase of (ii) with a primary detection agent in a solution followed by (iv) incubating the solid phase of (iii) with a secondary detection agent; and (v) detecting the presence of an agent on the solid phase with a detection system that measures, for example, UV, fluorescence, luminescence, calorimetric or other signal to detect the bound secondary detection agent.

In another embodiment of the invention, the Cell-based ELISA (C-ELISA) of the invention comprises (i) lysing cells and coating a solid surface with the cellular proteins released in situ in the lysis and coating buffer of the invention (five to ten minutes only are needed); (ii) blocking a solid phase with a blocking reagent dissolved in the blocking buffer of the invention (five minutes only are needed); (iii) incubating the solid phase of (ii) with a primary detection agent and a secondary detection agent; and (iv) detecting the presence of an agent on the solid phase with a detection system that measures, for example, UV, fluorescence, luminescence, colorimetric or other signal to detect the bound secondary detection agent.

In yet another embodiment of the invention, the Cell-based ELISA (C-ELISA) of the invention comprises (i) lysing cells and coating a solid surface with the cellular proteins released in situ in the lysis and coating buffer of the invention (five to ten minutes only are needed); (ii) blocking a solid phase with a blocking reagent dissolved in the blocking buffer of the invention (five minutes only are needed); (iii) incubating the solid phase of (ii) with a primary detection agent, a secondary detection agent and a tertiary detection agent in a solution; and (iv) detecting the presence of an agent on the solid phase with a detection system that measures, for example, UV, fluorescence, luminescence, calorimetric or other signal to detect the bound secondary or tertiary detection agent.

In the above-mentioned embodiments, those skilled in the art will know how to select a detection agent for a specific antigen. A detection agent can be, but is not limited to, a chemical molecule, a peptide molecule, a protein molecule, an RNA molecule, a DNA molecule, an antibody, a fragment of an antibody, a recombinant antibody, a bacteria cell, a virus particle, a cell, or a particle. One of the most commonly used detection agents is an antibody. Antibodies can be derived from different species, and they include, but are not limited to, rabbit, mouse, rat, sheep, goat, and chicken antibodies. Commercially available antibodies to a wide variety of antigens are known in the art.

Another one of the more commonly used detection agents comprise protein A, G, L, A/G or other antibody-binding polypeptides. These polypeptides can bind to the conserved region in an antibody. Yet another one of the most used detection agents is avidin or strepavidin. Avidin or streptavidin can bind to biotinylated antibodies or polypeptides. The detection agent in the above-mentioned embodiments can be a labeled detection agent or an unlabeled detection agent.

In the above-mentioned embodiments, those skilled in the art will know that there are a variety of labeling methods for a detection agent. The labeling methods include, but are not limited to, an enzyme such as horseradish peroxidase (HRP), alkaline phosphatase (AP), beta-galactosidase or other enzymes. A detection agent also can be labeled with radioactive isotopes of iodine or other isotopes. A detection agent also can be labeled by a fluorochrome (a fluorescent dye) that can be detected by fluorescence microscope or fluorometer or scanner or camera. A detection agent also can be labeled by a lumichrome which can be detected by luminescence methods. Alternatively, a detection agent also can be labeled by biotin, which can bind to avidin or streptavidin.

In the above-mentioned embodiments, those skilled in the art will be aware of different detection systems used in ELISAs that can be applied to the methods of the invention described herein. These detection systems include, but are not limited to, detection systems using chromogenic reactions of reporter enzymes such as horseradish peroxidase (HRP) and alkaline phosphatase (AP). The reporter enzymes can use different substrates for chromogenic detection. For example, HRP can use 4 CN (4-chloro-1-napthol), DAB/NiCl2 (3,3'-diaminobenzidine/NiCl2), or TMB as substrates for chromogenic detection.

In the above-mentioned embodiments, those skilled in the art will be aware of modifications to further improve the signal to noise ratio. These modifications include, but are not are limited to, adding one or multiple steps to the above embodiment.

Examples of blocking agents useful in the invention include, but are not limited to, non-fat milk, casein, BSA, or fish gelatin, or other chemical reagents. The pH of the working solution can be in the range of 10 to 14, typically 13.0.

The invention also provides kits comprising one or more components useful for performing an ELISA and instructions for carrying out a method of the invention. For example, such instructions can include methods for preparing a coating buffer and a blocking buffer of the invention. In another aspect, the kit may be compartmentalized to receive a coating buffer and/or a blocking buffer and one or more components for performing an ELISA.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The present invention is more particularly described in the following non-limiting examples, which are intended to be illustrative only, as numerous modifications and variations therein will be apparent to those skilled in the art.

Example I

Indirect ELISA for the Titration of Antibody

Figure 6:
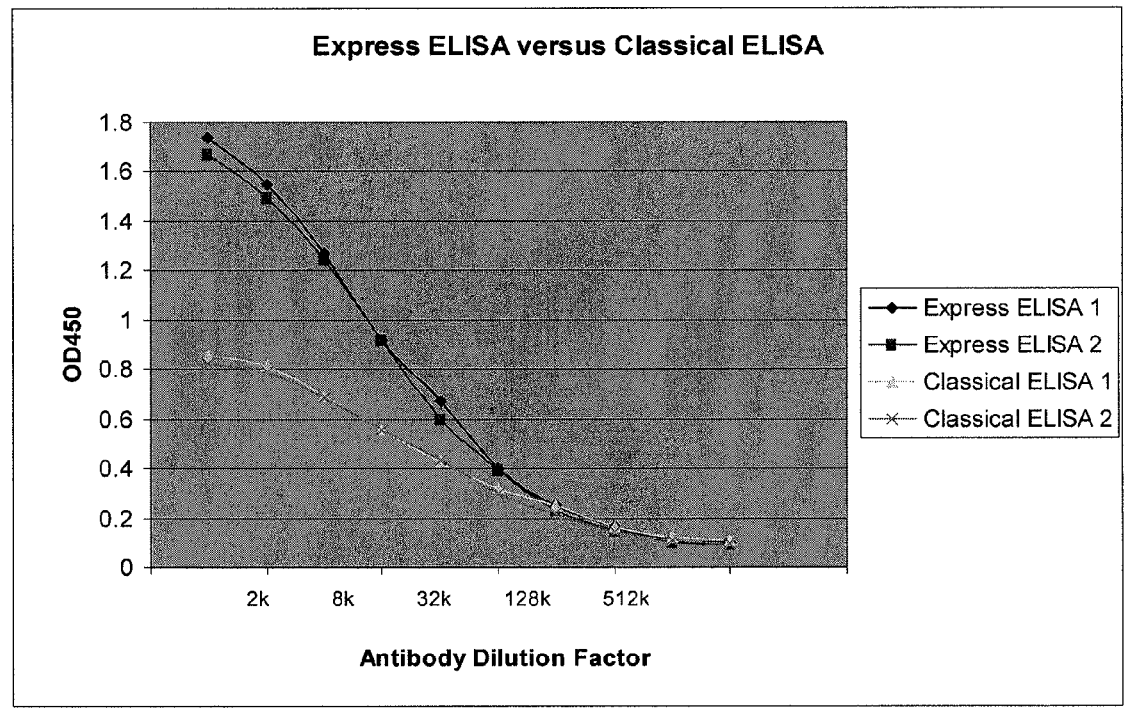
FIG. 6 shows an example of an indirect ELISA of the invention.

Purified GST protein (Genscript, Cat. No. Z02039) was coated on 96-well plates at 4 µg/ml following standard method (C and D) and the quick coating method of the invention (A and B), respectively. The plate was blocked following standard method (C and D) and the quick coating method of the invention (A and B), respectively. Rabbit anti GST serum was diluted and added to the plate wells for 1 hour at 37° C. for classic method, and 30 minutes at room temperature for the quick method of the invention. Plates were washed three times, Goat anti rabbit HRP (GenScript, Cat. A00098) was diluted 1:10000 and added to the plate wells for 1 hour at 37° C. for classic method, and 20 minutes at room temperature for the quick method of the invention. Finally the plate wells were washed and developed with TMB system (Genscript, Cat. No. M00078). The absorbance at 450 nm was measured using a microtiter plate spectrophotometer. The results are shown in FIG. 6.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for performing a rapid enzyme-linked immunosorbent assay (ELISA), comprising the steps of:
    (a) coating a solid phase with an antigen dissolved in a quick coating buffer for between about two to twenty minutes, wherein the quick coating buffer comprises water and a metal hydroxide selected from the group consisting of sodium hydroxide, potassium hydroxide and rubidium hydroxide;
    (b) blocking the solid phase with a blocking reagent dissolved in a quick blocking buffer for between about two to ten minutes, wherein the quick blocking buffer comprises a metal hydroxide selected from the group consisting of sodium hydroxide, potassium hydroxide and rubidium hydroxide; and
    (c) (i) incubating the solid phase with a primary detection agent in solution;
        washing the solid phase to remove any unbound primary detection agent; and
        detecting the presence of an agent bound on the solid phase with a detection system that detects the bound primary detection agent; or
    (ii) incubating the solid phase with a primary detection agent in solution;
        washing the solid phase to remove any unbound primary detection agent;
        incubating the solid phase with a secondary detection agent in solution;
        washing the solid phase to remove any unbound secondary detection agent; and
        detecting the presence of an agent bound on the solid phase with a detection system that detects the bound secondary detection agent; or
    (iii) incubating the solid phase simultaneously with a primary detection agent and a secondary detection agent in solution;
        washing the solid phase to remove any unbound primary detection agent and secondary detection agent; and
        detecting the presence of an agent bound on the solid phase with a detection system that detects the bound secondary detection agent; or
    (iv) incubating the solid phase with a primary detection agent in solution;
        washing the solid phase to remove any unbound primary detection agent; and
        incubating the solid phase with a secondary detection agent in solution;
        washing the solid phase to remove any unbound secondary detection agent; and
        incubating the solid phase with a tertiary detection agent in solution; and
        washing the solid phase to remove any unbound tertiary detection agent; and
        detecting the presence of an agent bound on the solid phase with a detection system that detects the bound tertiary detection agent; or
    (v) incubating the solid phase simultaneously with a primary detection agent, a secondary detection agent and a tertiary detection agent in solution;
        washing the solid phase to remove any unbound primary detection agent, secondary detection agent and tertiary detection agent; and
        detecting the presence of an agent bound on the solid phase with a detection system that detects the bound tertiary detection agent.

2. The method according to claim 1, wherein the solid phase is coated with an antigen in the quick coating buffer for about five minutes and the solid phase is blocked with the blocking reagent in the quick blocking buffer for about five minutes.

3. The method according to claim 1, wherein the blocking reagent is selected from the group consisting of non-fat milk, casein, BSA, fish gelatin and other chemical reagents.

4. The method according to claim 1, wherein said metal hydroxide concentration in the quick coating buffer ranges from between about 0.004 g/l to 40 g/l of buffer, and wherein the quick coating buffer has a pH ranging from between about 10.0 to 14.0.

5. The method according to claim 4, wherein the metal hydroxide in the quick coating buffer is sodium hydroxide.

6. The method according to claim 5, wherein the sodium hydroxide concentration is about 4 g/l of buffer, and wherein the quick coating buffer has a pH of about 13.0.

7. The method according to claim 1, wherein said metal hydroxide a concentration in the quick blocking buffer ranges from between about 0.0056 g/l to 56 g/l of buffer, and wherein the quick blocking buffer has a pH ranging from between about 10.0 to 14.0.

8. The method according to claim 7, wherein the metal hydroxide in the quick blocking buffer is potassium hydroxide.

9. The method according to claim 8, wherein the potassium hydroxide concentration is about 5.6 g/l of buffer, and wherein the quick blocking buffer has a pH of about 13.0.

10. The method according to claim 1, wherein said detection system detects the bound detection agent by measuring signals selected from the group consisting of ultraviolet light, fluorescence, luminescence, colorimetric signals and other signals capable of detecting the bound detection agent.

11. The method according to claim 1, wherein the detection agent can be labeled or unlabeled, said detection agent selected from the group consisting of avidin, strepavidin, a chemical molecule, a peptide molecule, a protein molecule, an RNA molecule, a DNA molecule, an antibody, a fragment of an antibody, a recombinant antibody, a bacterial cell, a virus particle, a cell and a particle.

12. The method according to claim 11, wherein the protein molecule is selected from the group consisting of protein A, protein G, protein L, protein A/G and other antibody-binding polypeptides.

13. The method according to claim 11, wherein the detection agent is labeled, said label is selected from the group consisting of an enzyme; radioactive isotope; fluorochrome; lumichrome and biotin.

14. The method according to claim 13, wherein the enzyme is selected from the group consisting of horseradish peroxidase, alkaline phosphatase and beta-galactosidase.

* * * * *